United States Patent
Zhang et al.

(10) Patent No.: US 7,869,032 B2
(45) Date of Patent: Jan. 11, 2011

(54) BIOSENSORS WITH POROUS DIELECTRIC SURFACE FOR FLUORESCENCE ENHANCEMENT AND METHODS OF MANUFACTURE

(75) Inventors: Wei Zhang, Urbana, IL (US); Brian T. Cunningham, Champaign, IL (US)

(73) Assignee: The Board of Trustees of the University of Illinois, Urbana, IL (US)

(*) Notice: Subject to any disclaimer, the term of this patent is extended or adjusted under 35 U.S.C. 154(b) by 430 days.

(21) Appl. No.: 12/079,171

(22) Filed: Mar. 24, 2008

(65) Prior Publication Data

US 2008/0246961 A1    Oct. 9, 2008

Related U.S. Application Data

(60) Provisional application No. 60/910,315, filed on Apr. 5, 2007.

(51) Int. Cl.
*G01J 3/30* (2006.01)
(52) U.S. Cl. .................... 356/317; 356/311
(58) Field of Classification Search ................ 356/317, 356/328, 445, 364, 301, 311, 305; 156/60; 65/386; 422/82.05–82.11; 385/12, 37; 435/7.9, 435/7.32, 287.2, 7.2, 5, 4, 7.1, 34, 288.7; 438/31, 32, 69, 71, 72, 87; 436/518, 164, 436/525, 527, 805; 977/924; 372/102, 7
See application file for complete search history.

(56) References Cited

U.S. PATENT DOCUMENTS

| | | | |
|---|---|---|---|
| 5,216,680 A | 6/1993 | Magnusson et al. ............ 372/20 |
| 6,990,259 B2 | 1/2006 | Cunningham ................. 385/12 |
| 7,094,595 B2 | 8/2006 | Cunningham et al. ..... 435/287.2 |
| 7,118,710 B2 | 10/2006 | Cunningham ............ 422/82.09 |
| 7,167,615 B1 | 1/2007 | Wawro et al. ................. 385/37 |
| 7,400,399 B2 | 7/2008 | Wawro et al. ............... 356/328 |
| 2002/0127565 A1 | 9/2002 | Cunningham et al. .......... 435/6 |
| 2003/0026891 A1 | 2/2003 | Qui et al. ...................... 427/58 |
| 2003/0027327 A1 | 2/2003 | Cunningham et al. .... 435/287.2 |
| 2003/0059855 A1 | 3/2003 | Cunningham et al. ........ 435/7.9 |

(Continued)

OTHER PUBLICATIONS

Y. J. Hung, I. I. Smolyaninov, C. C. Davis, and H. C. Wu, "Fluorescence enhancement by surface gratings," *Optics Express*, vol. 14, pp. 10825-10830, 2006.

(Continued)

*Primary Examiner*—Gregory J Toatley
*Assistant Examiner*—Tri T Ton
(74) *Attorney, Agent, or Firm*—McDonnell Boehnen Hulbert & Berghoff LLP

(57) ABSTRACT

Biosensors are disclosed which include a surface for binding to sample molecule to the biosensor in the form of a porous, thin film of dielectric material, e.g., $TiO_2$. In one example the porous, thin film is in the form of a multitude of sub-micron sized rod-like structures ("nanorods") projecting therefrom. In one embodiment, the biosensor is in the form of a photonic crystal biosensor. The approach of depositing a thin film of dielectric nanorods may be applied to any enhanced fluorescence biosensor surface structure, including 1-dimensional photonic crystals, 2-dimensional photonic crystals, 3-dimensional photonic crystals, surface plasmon resonance surfaces, planar waveguides, and grating-coupled waveguides. The dielectric nanorod structures can be fabricated on the surface of a biosensor by the glancing angle deposition technique (GLAD).

21 Claims, 5 Drawing Sheets

U.S. PATENT DOCUMENTS

| | | | |
|---|---|---|---|
| 2006/0252065 A1 | 11/2006 | Zhao et al. | 435/6 |
| 2006/0281077 A1 | 12/2006 | Lin et al. | 435/5 |
| 2007/0009380 A1 | 1/2007 | Cunningham | 422/58 |
| 2007/0009968 A1 | 1/2007 | Cunningham et al. | 435/7.9 |
| 2007/0015151 A1 | 1/2007 | Schrenzel et al. | 435/6 |

OTHER PUBLICATIONS

T. Hayakawa, S. T. Selvan, and M. Nogami, "Field enhancement effect of small Ag particles on the fluorescence from Eu3+-doped SiO2 glass," *Applied Physics Letters*, vol. 74, pp. 1513-1515, 1999.

K. Asian, S. N. Malyn, and C. D. Geddes, "Metal-enhanced fluorescence from gold surfaces: Angular dependent emission," *Journal of Fluorescence*, vol. 17, pp. 7-13, 2007.

K. Aslan, I. Gryczynski, J. Malicka, E. Matveeva, J. R. Lakowicz, and C. D. Geddes, "Metal-enhanced fluorescence: an emerging tool in biotechnology," *Current Opinion in Biotechnology*, vol. 16, pp. 55-62, 2005.

W. Budach, D. Neuschafer, C. Wanke, and S. D. Chibout, "Generation of transducers for fluorescence-based microarrays with enhanced sensitivity and their application for gene expression profiling," *Analytical Chemistry*, vol. 75, No. 11, pp. 2571-2577, 2003.

P. C. Mathias, N. Ganesh, L. L. Chan, and B. T. Cunningham, "Combined enhanced fluorescence and label-free biomolecular detection with a photonic crystal surface," *Applied Optics*, vol. 46, No. 12, pp. 2351-2360, 2007.

N. Ganesh, W. Zhang, P. C. Mathias, E. Chow, J. A. N. T. Soares, V. Malyarchuk, A. D. Smith, and B. T. Cunningham, "Enhanced fluorescence emission from quantum dots on a photonic crystal surface," *Nature Nanotechnology*, vol. 2, pp. 515-520, 2007.

N. Ganesh and B. T. Cunningham, "Photonic-crystal near-ultraviolet reflectance filters fabricated by nanoreplica molding," *Applied Physics Letters*, vol. 88, pp. 071110-1-071110-3 2006.

C. J. Choi and B. T. Cunningham, "Single-step fabrication and characterization of photonic crystal biosensors with polymer microfluidic channels," *Lab on a Chip*, vol. 6, pp. 1373-1380, 2006.

B. T. Cunningham, P. Li, S. Schulz, B. Lin, C. Baird, J. Gerstenmaier, C. Genick, F. Wang, E. Fine, and L. Laing, "Label-free assays on the BIND system," *Journal of Biomolecular Screening*, vol. 9, pp. 481-490, 2004.

S. S. Wang, R. Magnusson, J. S. Bagby, and M. G. Moharam, "Guided-Mode Resonances in Planar Dielectric-Layer Diffraction Gratings," *Journal of the Optical Society of America-Optics Image Science and Vision*, vol. 7, No. 8, pp. 1470-1474, 1990.

R. Magnusson and S. S. Wang, "New Principle for Optical Filters," *Applied Physics Letters*, vol. 61, No. 9, pp. 1022-1024, 1992.

S. S. Wang and R. Magnusson, "Theory and Applications of Guided-Mode Resonance Filters," *Applied Optics*, vol. 32, No. 14, pp. 2606-2613, 1993.

C. Y. Wei, S. J. Liu, D. G. Deng, J. Shen, J. D. Shao, and Z. X. Fan, "Electric field enhancement in guided-mode resonance filters," *Optics Letters*, vol. 31, No. 9, pp. 1223-1225, 2006.

Cunningham, B.T., P. Li, B. Lin and J. Pepper, "Colorimetric Resonant Reflection as a Direct Biochemical Assay Technique," *Sensor and Actuators B*, vol. 81, pp. 316-328, 2002.

Cunningham, B.T.J. Qiu, P. Li, J. Pepper and B. Hugh, "A Plastic Calorimetric Resonant Optical Biosensor for Multiparallel Detection of Label Free Biochemical Interactions," *Sensors and Actuators B*, vol. 85, pp. 219-226, 2002.

J. G. W. v. d. Waterbeemd and G. W. v. Oosterhout, "Effect of the Mobility of Metal Atoms on the Structure of Thin Films Deposited at Oblique Incidence," *Philips Res. Rep.*, vol. 22, pp. 375-387, 1967.

K. Robbie, L. J. Friedrich, S. K. Dew, T. Smy, and M. J. Brett, "Fabrication of Thin-Films with Highly Porous Microstructures," *Journal of Vacuum Science & Technology A-Vacuum Surfaces and Films*, vol. 13, pp. 1032-1035, 1995.

L. Abelmann and C. Lodder, "Oblique evaporation and surface diffusion," *Thin Solid Films*, vol. 305, pp. 1-21, 1997.

Lin et al., *A Porous Silicon-Based Optical Interferometric Biosensor*, Science vol. 278, pp. 840-844 (1997).

Wang et al., "Glucose oxidase entrapped in polypyrrole on high-surface-area Pt electrodes: a model platform for sensitive electroenzymatic biosensors," *Journal of Electroanalytical Chemistry*, vol. 575, pp. 139-146, 2005.

Zhao et al., "Designing Nanostructures by Glancing Angle Deposition", Proceedings of SPIE (online), vol. 5219, Nanotubes and Nanowires, pp. 59-73 (SPIE, Bellingham, WA).

International Search Report and Written Opinion in PCT/US28/03854, dated Jul. 1, 2008.

Wawro et al., *Optical Fiber Endface Biosensor Based on Resonances in Dielectric Waveguide Gratings*, International Biomedical Optics Symposium Jan. 2000, Proceedings SPIE, vol. 3911, pp. 86-94 (2000).

International Preliminary Examination Report dated Oct. 15, 2009 in PCT/US2008/003854, filed Mar. 24, 2008.

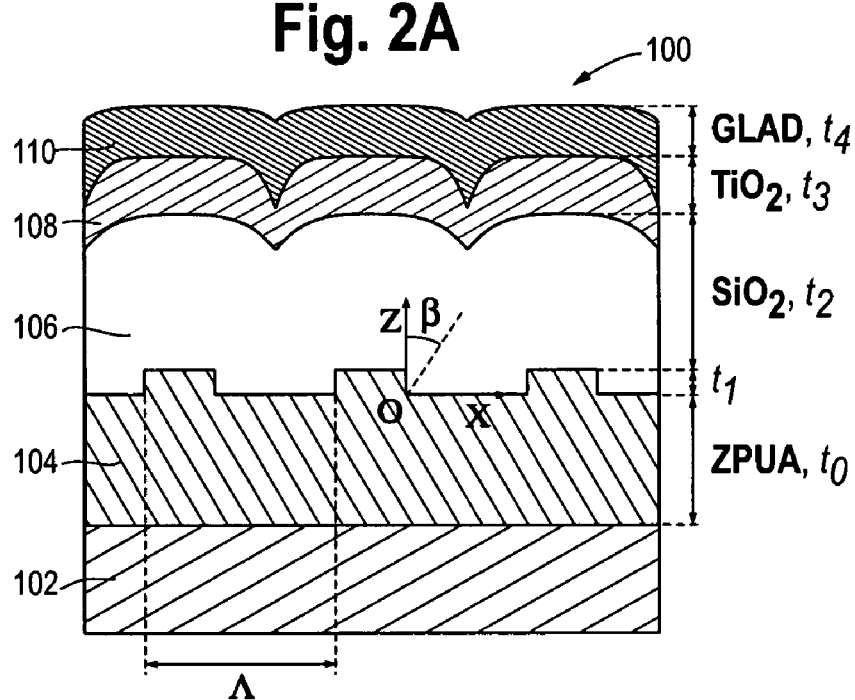
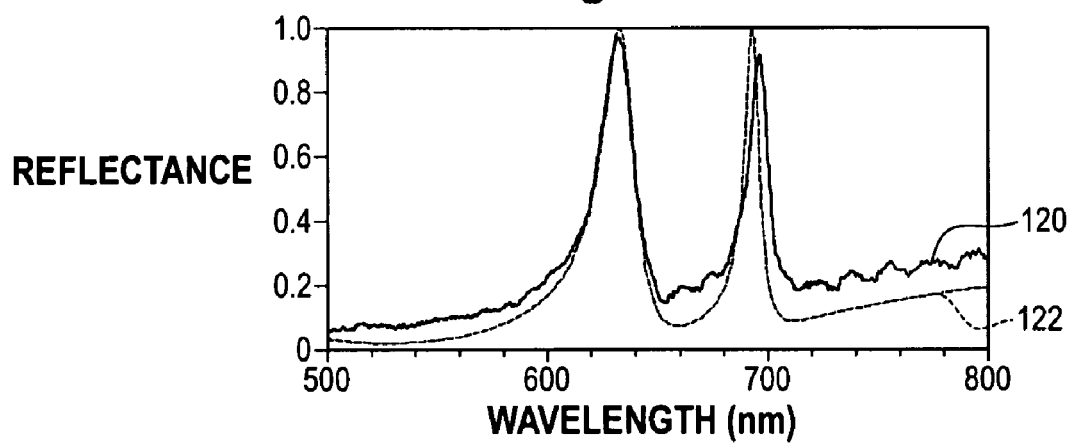

BIOSENSORS WITH POROUS DIELECTRIC SURFACE FOR FLUORESCENCE ENHANCEMENT AND METHODS OF MANUFACTURE

PRIORITY

This application claims priority benefits under 35 U.S.C. §119(e) to U.S. provisional application Ser. No. 60/910,315 filed Apr. 5, 2007, the content of which is incorporated by reference herein.

STATEMENT REGARDING FEDERALLY SPONSORED RESEARCH OR DEVELOPMENT

This invention was made, at least in part, with United States governmental support awarded by the National Science Foundation under NSF BES 0427657. The United States Government has certain rights in this invention.

BACKGROUND

Fluorescence has long been recognized as an important tool for probing biological structure and function. Development of optically active structures that can enhance fluorescence intensity have gained much attention as a means for detecting fluorescent-tagged analytes at low concentrations for applications in DNA expression analysis and protein diagnostic assays. The majority of structures developed to date for this purpose utilize plasmonics of metals to increase the excitation of fluorophores through enhanced near fields, to increase the quantum yield by increasing the intrinsic radiative decay rate of the fluorophores, to increase the directional emission or to employ some combination of these processes. Background references include Y. J. Hung, I. I. Smolyaninov, C. C. Davis, and H. C. Wu, "Fluorescence enhancement by surface gratings," *Optics Express*, vol. 14, pp. 10825-10830, 2006; T. Hayakawa, S. T. Selvan, and M. Nogami, "Field enhancement effect of small Ag particles on the fluorescence from Eu3+-doped SiO2 glass," *Applied Physics Letters*, vol. 74, pp. 1513-1515, 1999; K. Aslan, S. N. Malyn, and C. D. Geddes, "Metal-enhanced fluorescence from gold surfaces: Angular dependent emission," *Journal of Fluorescence*, vol. 17, pp. 7-13, 2007; K. Aslan, I. Gryczynski, J. Malicka, E. Matveeva, J. R. Lakowicz, and C. D. Geddes, "Metal-enhanced fluorescence: an emerging tool in biotechnology," *Current Opinion in Biotechnology*, vol. 16, pp. 55-62, 2005. Another reference of interest is W. Budach, D. Neuschafer, C. Wanke, and S. D. Chibout, "Generation of transducers for fluorescence-based microarrays with enhanced sensitivity and their application for gene expression profiling," *Analytical Chemistry*, vol. 75, pp. 2571-2577, 2003 which discloses dielectric gratings for detection of fluorescence-labeled samples.

Recently, photonic crystal (PC) sensors have also been used to enhance the emission intensity of fluorophores and quantum dots. Photonic crystals, also commonly referred to as photonic bandgap structures, are periodic dielectric structures exhibiting a spatially periodic variation in refractive index that forbids propagation of certain frequencies of incident electromagnetic radiation. The photonic band gap of a photonic crystal refers to the range of frequencies of electromagnetic radiation for which propagation through the structure is prevented. The photonic band gap phenomenon may be conceptualized as complete reflection of incident electromagnetic radiation having selected frequencies due to interaction with the periodic structural domains of a photonic crystal. The spatial arrangement and refractive indices of these structural domains generate photonic bands gaps that inhibit propagation of electromagnetic radiation centered about a particular frequency.

Photonic crystals provide an electromagnetic analog to electron-wave behavior observed in crystals wherein electron-wave concepts, such as dispersion relations, Bloch wave functions, van Hove singularities and tunneling, having electromagnetic counterparts in photonic crystals. In semiconductor crystals, for example, an electronic band gap of energy states for which electrons are forbidden results from a periodic atomic crystalline structure. By analogy, in a photonic crystal, a photonic band gap of forbidden energies (or wavelengths/frequencies) of electromagnetic radiation results from a periodic structure of a dielectric material, where the periodicity is of a distance suitable to interact with incident electromagnetic radiation.

Selection of the physical dimensions, refractive indices and spatial distribution of structural domains of a photonic crystal provides an effective means of designing a photonic crystal a photonic band gap with a selected frequency distribution. One-dimensional, two-dimensional and three-dimensional photonic crystals have been fabricated providing complete or at least partial photonic band having selected frequency distributions gaps in one or more directions and/or polarizations of light. Photonic crystals have also been fabricated having selected local disruptions (e.g., missing or differently-shaped portions of the structural domains of periodic array) in their periodic structure, thereby generating defect cavity modes with frequencies within a forbidden bandgap of the crystal. (See Cunningham, U.S. Pat. No. 6,990,259). Photonic crystals having specific defects are of particular interest because they provide optical properties useful for controlling and manipulating electromagnetic radiation, such as the ability to provide optical confinement and/or wave guiding with very little, or substantially no, radiative losses.

As diffraction and optical interference processes give rise to the photonic band gap phenomenon, the periodicity of photonic crystal structures is typically on the order of the wavelength of incident electromagnetic radiation. Accordingly, photonic crystals for controlling and manipulating visible and ultraviolet electromagnetic radiation typically comprise dielectric structures with periodic structural domains having submicron physical dimensions on the order of 100s of nanometers. A number of fabrication pathways for making periodic structures having these physical dimensions have been developed over the last decade, including micromachining and nanomachining techniques (e.g., lithographic patterning and dry/wet etching, electrochemical processing etc.), colloidal self assembly, replica molding, layer-by-layer assembly and interference lithography. Advances in these fabrication techniques have enabled fabrication of one-dimensional, two-dimensional and three-dimensional photonic crystals from a range of materials including dielectric crystals, polymers and colloidal materials.

Because PC sensors are comprised of dielectric materials, they will not quench fluorophores within <30 nm of their surface by resonant energy transfer, and they can exhibit high Q-factors due to their low absorption loss. Typically comprised of a one-dimensional (1D) or two-dimensional (2D) periodic surface structure formed from a low refractive index (RI) dielectric material that is overcoated with a high RI thin film, these devices can be fabricated upon plastic substrates inexpensively over large areas by a nanoreplica molding process and incorporated into the surface of glass slides, microfluidic channels, and microtiter plates. The device period, grating depth, film thicknesses, and RIs of the materials are chosen in such a way that the PCs can support guided-mode resonances at designated wavelengths, where the device reflects ~100% of incident light at the resonant wavelengths with all other wavelengths being transmitted. Under resonant conditions, excited leaky modes are localized in space during their finite lifetimes, which enhances the near electric-field intensity of the PC structure and thus enhances the excitation of fluorophores near the PC surface.

A representative photonic crystal sensor having a one dimensional periodic surface grating structure and its associated detection instrument is shown in FIG. 1. The PC sensor 1 consists of a substrate polyester sheet 10, a periodic surface grating structure 12 formed on the substrate 10 in the form of alternating high and low regions, and a high index of refraction ($TiO_2$) material 14 deposited on the grating structure 12. The device is interrogated with white light from a light source (not shown) that is coupled to an illuminating fiber 16 of a fiber optic probe 18. The illuminating light is passed through a collimating lens 20 and is incident on the PC sensor 1. A narrow band of reflected light is captured by a detecting fiber 26 of the probe 18. The reflected light is passed to a spectrometer 28. Binding of a sample in a sample medium (which may be air or water) causes a shift in the peak wavelength value of the reflected light, with the amount of the shift being a measure of the amount of binding to the surface of the sensor.

Further background information relating to photonic crystals sensors and their properties and methods of manufacture are disclosed in the following references, which are incorporated by reference herein: P. C. Mathias, N. Ganesh, L. L. Chan, and B. T. Cunningham, "Combined enhanced fluorescence and label-free biomolecular detection with a photonic crystal surface," *Applied Optics*, vol. 46, pp. 2351-2360, 2007; N. Ganesh, W. Zhang, P. C. Mathias, E. Chow, J. A. N. T. Soares, V. Malyarchuk, A. D. Smith, and B. T. Cunningham, "Enhanced fluorescence emission from quantum dots on a photonic crystal surface," *Nature Nanotechnology*, vol. 2, pp. 515-520, 2007; N. Ganesh and B. T. Cunningham, "Photonic-crystal near-ultraviolet reflectance filters fabricated by nanoreplica molding," *Applied Physics Letters*, vol. 88, 2006; C. J. Choi and B. T. Cunningham, "Single-step fabrication and characterization of photonic crystal biosensors with polymer microfluidic channels," *Lab on a Chip*, vol. 6, pp. 1373-1380, 2006; B. T. Cunningham, P. Li, S. Schulz, B. Lin, C. Baird, J. Gerstenmaier, C. Genick, F. Wang, E. Fine, and L. Laing, "Label-free assays on the BIND system," *Journal of Biomolecular Screening*, vol. 9, pp. 481-490, 2004; S. S. Wang, R. Magnusson, J. S. Bagby, and M. G. Moharam, "Guided-Mode Resonances in Planar Dielectric-Layer Diffraction Gratings," *Journal of the Optical Society of America a-Optics Image Science and Vision*, vol. 7, pp. 1470-1474, 1990; R. Magnusson and S. S. Wang, "New Principle for Optical Filters," *Applied Physics Letters*, vol. 61, pp. 1022-1024, 1992; S. S. Wang and R. Magnusson, "Theory and Applications of Guided-Mode Resonance Filters," *Applied Optics*, vol. 32, pp. 2606-2613, 199; C. Y. Wei, S. J. Liu, D. G. Deng, J. Shen, J. D. Shao, and Z. X. Fan, "Electric field enhancement in guided-mode resonance filters," *Optics Letters*, vol. 31, pp. 1223-1225, 2006.

Given substantial advances in their fabrication and their unique optical properties, photonic crystal-based sensors have been recently developed for a range of biosensing applications. To operate as a biosensor, a photonic crystal is provided in a configuration such that its active area is exposed to a fluid containing analytes for detection. The presence of analyte proximate to the photonic crystal sensor modulates the resonant coupling of light into the crystal, thereby resulting in a measurable change in the wavelength distribution of electromagnetic radiation transmitted, scattered or reflected by the crystal resulting from changes in the photonic band gap of the crystal. The highly localized nature of the confined electromagnetic field generated by the crystal ensures that that detection via photonic crystal based sensors is restricted to a probe region proximate to the active area of the sensor (that is, generally less than 400 nm from the surface). In typical sensing applications, a read out system is used wherein polarized electromagnetic radiation having a selected wavelength distribution is provided to the photonic crystal and subsequently reflected or transmitted electromagnetic radiation is frequency analyzed by an appropriate photodetector, such as a spectrometer in combination with an appropriate detector. By observing and/or quantifying the change in wavelength distribution resulting from interaction of the fluid and the photonic crystal, analytes in the probe region are detected and/or analyzed. Biosensors incorporating photonic crystal structures are described in the following references which are hereby incorporated by reference in their entireties: U.S. Pat. Nos. 7,118,710, 7,094,595, and 6,990,259; U.S. Published applications 2007/0009968; 2002/0127565; 2003/0059855; 2007/0009380; 2003/0027327; and Cunningham, B. T., P. Li, B. Lin and J. Pepper, Colorimetric Resonant Reflection as a Direct Biochemical Assay Technique, Sensor and Actuators B, 2002, 81, pgs 316-328; and Cunningham, B. T. J. Qiu, P. Li, J. Pepper and B. Hugh, A Plastic Calorimetric Resonant Optical Biosensor for Multi-parallel Detection of Label Free Biochemical Interactions, Sensors and Actuators B, 2002, 85, pgs 219-226.

Advantages provided by photonic crystals for biosensing include the ability to detect and characterize a wide range of materials, including peptides, proteins, oligonucleotides, cells, bacteria and virus particles, without the use of labels, such as fluorescent labels and radioligands, or secondary reporter systems. Direct detection provided by photonic crystal sensing enhances ease of implementation of these techniques by eliminating labor intensive processing required to synthetically link and/or read out a label or reporter system. This beneficial aspect of photonic crystal-based sensing also eliminates a significant source of experimental uncertainty arising from the influence of a label or reporter system on molecular conformation, reactivity, bioactivity and/or kinetics; and eliminates problems arising from liquid phase fluorescence quenching processes. Photonic crystal based sensors are also compatible with functionalization, for example by incorporation of biomolecules and/or candidate therapeutic molecules bound to the surface of the active area of the photonic crystal structure; a capability which is particularly attractive for selectively detecting specific target molecules for screening and biosensing applications. Other benefits provided by photonic crystal approaches to biosensing include: (i) good sensitivity and image resolution; (ii) compatibility with relatively straightforward optical readout systems, (iii) and the ability to provide highly localized detection useful for multichannel systems having a high area density of independent sensor channels. As a result of these attributes, photonic crystal based sensors are emerging as a major tool for selective biochemical detection and analysis in diverse fields including genomics, proteomics, pharmaceutical screening and biomedical diagnostics.

Even with these advances, the sensitivity of the sensors limits their applications. Development of sensor designs that enhance sensitivity is especially important because it allows detection of lower concentration of analytes and detection of small molecules with higher signal-to-noise ratio.

Previously, enhancement of optical biosensor sensitivity has been achieved through the use of polymer hydrogels such as dextran to extend the surface area for ligand attachment into a 3-dimensional volume within the evanescent field region of surface plasma resonance (SPR) sensors. Although hydrogel films offer a high surface area for covalent attachment of biomolecules, disadvantages of this method include (1) the hydrogel film is not an integral part of the device, (2) it involves a complex procedure for deposition and functionalization using liquid-based processes, and (3) as a polymer based on a sugar monomer, the dextran layer is subject to swelling and/or dissociation by extremes in pH. Therefore, enhancement of biosensor surface area using a more chemically and mechanically robust system is needed.

Glancing angle deposition (GLAD) is a physical vapor deposition technique in which the angle between the incoming flux and the surface of the substrate is set to be typically less than 15°. The technique is described in the following references, incorporated by reference herein: J. G. W. v. d. Waterbeemd and G. W. v. Oosterhout, "Effect of the Mobility of Metal Atoms on the Structure of Thin Films Deposited at Oblique Incidence," *Philips Res. Rep.*, vol. 22, pp. 375-387, 1967; K. Robbie, L. J. Friedrich, S. K. Dew, T. Smy, and M. J. Brett, "Fabrication of Thin-Films with Highly Porous Microstructures," *Journal of Vacuum Science & Technology a-Vacuum Surfaces and Films*, vol. 13, pp. 1032-1035, 1995. L. Abelmann and C. Lodder, "Oblique evaporation and surface diffusion," *Thin Solid Films*, vol. 305, pp. 1-21, 1997.

Embodiments described below include biosensors with nanorod structures to enhance the surface area of the PC sensor, with the nanorod structures created using the GLAD technique.

SUMMARY

In a first aspect, biosensors are described which have an enhanced surface area due to a porous dielectric structure in the form of a thin film of dielectric material deposited on the surface of the sensor. As used herein, a "porous dielectric structure" is a layer formed from one or more dielectric materials, where the layer contains "holes" or gaps between structures of the dielectric material. In one example, the porous dielectric structure is in the form of a multitude of sub-micron sized rod-like structures ("nanorods") deposited on the sensor surface and projecting therefrom. The nanorods are deposited on the sensor surface using the glancing angle deposition (GLAD) technique described above. An example is shown in FIGS. 3A and 3B. The dielectric material forming the porous dielectric structure is preferably a relatively high index of refraction material such as $TiO_2$ with an index of refraction n being greater than that of water. Other dielectric materials can be used for the porous dielectric structure, and preferred materials are dielectric material with low optical loss coefficient at the resonant wavelength of the photonic crystal. Examples include $Ta_2O_5$, SiN, $SiO_2$, ZnS, MgF, VO and $HfO_2$.

With the photonic crystal sensors of this disclosure, the emission intensity of a fluorescent dye-labeled sample applied to the sensor can be increased by over two orders of magnitude through the combined effects of enhanced near fields produced by a 1-dimensional or 2-dimensional photonic crystal slab and the enhanced surface area provided by the nanorod structure porous dielectric (e.g., $TiO_2$) film that is deposited on top of the photonic crystal surface. Rigorous coupled-wave analysis shows that the porous $TiO_2$ film serves to shift the location of resonant leaky modes more fully into the volume in which biomolecular binding can take place, thus resulting in sensitivity gains that are greater than only the increase in available surface area.

The extent to which porous high index of refraction films may enhance fluorescence detection sensitivity has been explored and experimentally confirmed by varying the film thickness and detection of streptavidin labeled with the organic fluorophore cyanine-5 (Cy-5) resulting in a maximum demonstrated enhancement of 114× compared to detection on an unpatterned glass substrate. The approach may be applied to the enhancement of the excitation of any fluorescent dye, including semiconductor quantum dots, organic dyes, and fluorescent proteins. The approach of applying a porous dielectric structure to the surface of a biosensor may also be applied to any enhanced fluorescence detection on a variety of different biosensor surfaces, including 1-dimension photonic crystals, 2-dimensional photonic crystals, 3-dimensional photonic crystals, surface plasmon resonance surfaces, planar waveguides, and grating-coupled waveguides.

The biosensors of this disclosure increase the sensitivity of fluorophore detection by as much as a factor of >100× compared to the sensitivity of a biosensor that does not use the invention. This increase in sensitivity has several advantages. For example, the sensors can be used for detection of fluorescent tags to quantify the presence and/or concentration of specific DNA sequences, protein biomarkers, virus particles, cells, bacteria, and other biochemical analytes in a test sample. Greater sensitivity is used in gene expression analysis to identify the presence of genes that are expressed at low concentrations and in protein detection to measure the presence of molecules that correlate with the presence of disease at lower concentrations than are measurable otherwise.

In use, the sample molecule is labeled with a fluorescent material, such as quantum dot or organic fluorescent dye. In a photonic crystal embodiment, the emission intensity of the fluorescent material is increased by over two orders of magnitude through the combined effects of enhanced near fields produced by the photonic crystal and the enhanced surface area provided by the nanorod-structured dielectric film that is deposited on top of the photonic crystal surface. The porous $TiO_2$ film serves to shift the location of resonant leaky modes of the photonic crystal more fully into the volume in which biomolecular binding can take place, thus resulting in sensitivity gains that are greater than only the increase in available surface area. Additionally, addition of the nanorod films can reduce the photonic crystal resonance linewidth, or in other words the Q-factor for the resonance becomes higher. This is due to an increase in the strength of the enhanced electric field in the region where binding to the sensor surface occurs.

In preferred embodiments, the porous dielectric structures are fabricated on the surface of a biosensor by the glancing angle deposition technique (GLAD). The GLAD deposition technique always produces a random coating of isolated structures extending from the sites of deposition nucleation on the substrate surface. If the substrate is not rotated during deposition, the growth will be in the form of rods that will be oriented at an angle to the substrate surface. However, rotation of the substrate during deposition can produce a wide variety of shapes, depending on the ratio between the deposition rate and the substrate rotation rate. Therefore, the "nanorods" can take the form of helical structures, step-wise spiral staircase structures, diagonal zig-zags, and others. It is also possible to alternate the dielectric deposition technique in the process of building up the porous dielectric structure between GLAD growth and ordinary growth to make structures that have nanorods that are capped with a flat top (like a mushroom) or a small spheroid. One could even change back to GLAD growth to make "dumbbell" structures. The term "nanorods" is intended to be interpreted in this document to cover all such isolated structures extending from the surface of the biosensor, whether cylindrical, spiral, zig-zag or otherwise, including such isolated structures with caps or other features at the ends thereof or in portions intermediate the base of the structure and the end of the structure.

In still another aspect, methods of detection of a sample are described, comprising the steps of: a) providing a sample having a fluorescent label bound to the sample; b) placing the sample onto a photonic crystal biosensor as described in this disclosure having a porous dielectric surface; c) illuminating the biosensor with light that excites the fluorescent label and capturing fluorescent emission from the sensor with a detection instrument; and d) determining the intensity of the fluorescence emission from the sensor. The illuminating step involves use of an optical source such as a laser, LED, mercury vapor lamp, or tungsten halogen lamp. The fluorescent emission from the fluorescent label is at a higher wavelength which is detected with a photomultiplier tube, imaging camera, or some other photon detection device. In a representative embodiment, the sample comprises a biological sample, e.g., DNA sample, virus, protein or protein fragment, etc. The sample can be labeled with any suitable fluorophore, such as an organic fluorophore or a luminescent semiconductor material known in the art as a "quantum dot."

BRIEF DESCRIPTION OF THE DRAWINGS

FIG. 2A is cross sectional view of a one-dimensional photonic crystal sensor with a thin film porous dielectric structure on the upper surface of the sensor in accordance with a representative and non-limiting embodiment.

FIG. 2B is a plot of the measured and simulated reflection spectrum of the device of FIG. 2A with TE polarized light incident on the device at an incident angle β of 6 degrees from normal incidence.

DETAILED DESCRIPTION

Figure 1:
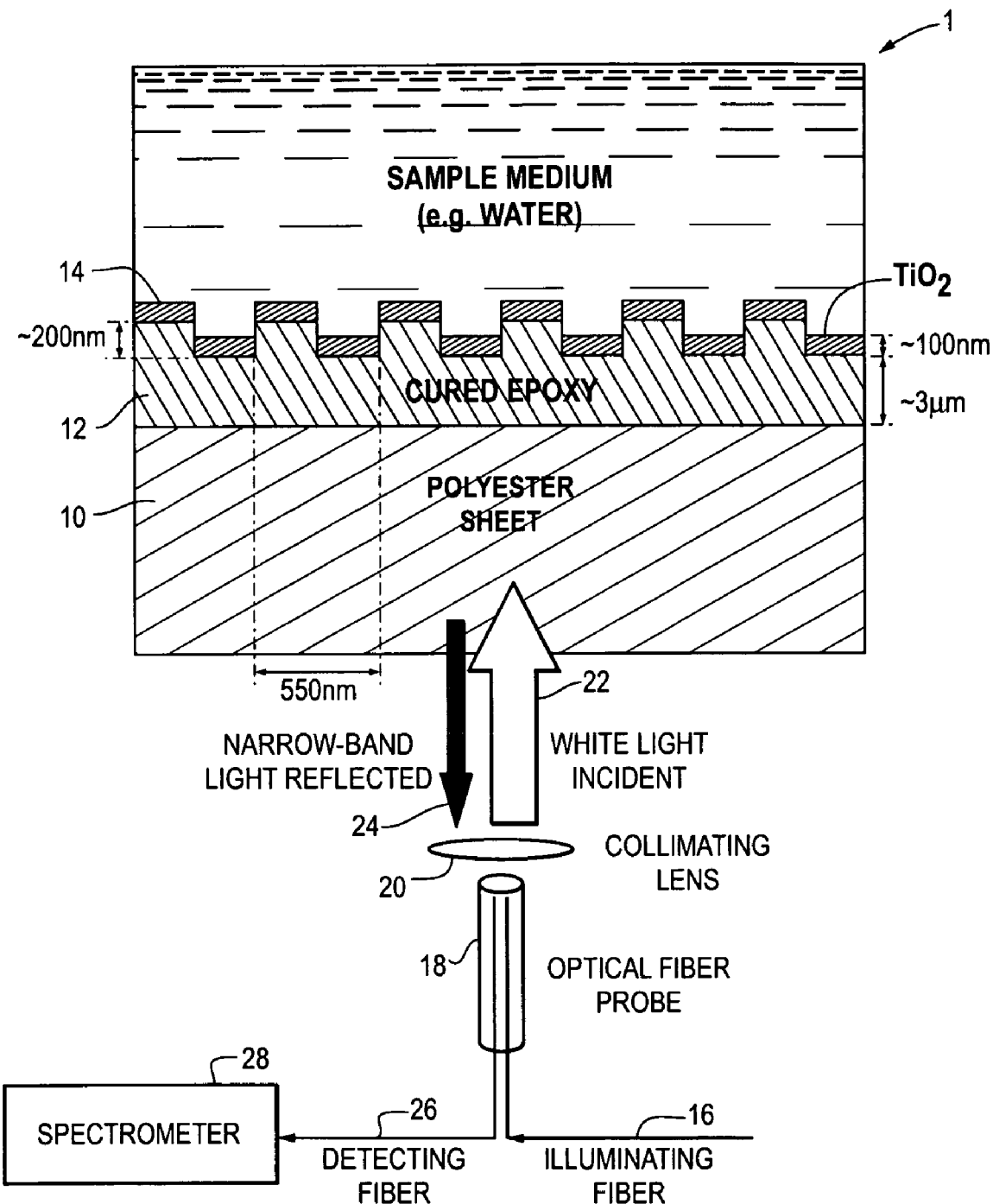
FIG. 1 is a cross-sectional view of a prior art photonic crystal biosensor having a one dimensional surface grating structure showing the structure of the sensor and the readout instrumentation. The sensor is illuminated at normal incidence with collimated white light through an optical fiber probe. The sensor reflects back only a narrow band of wavelengths, centered around a peak wavelength value (PWV). The reflected spectrum is measured by a spectrometer that determines shifts in PWV due to biochemical binding on the sensor surface.

Biosensors are disclosed which include a surface for binding of a sample molecule to the biosensor in the form of a porous dielectric structure in the form of a thin film of dielectric material, e.g., $TiO_2$. In one example the porous, thin film is in the form of a multitude of sub-micron sized rod-like structures ("nanorods") projecting from the surface of the sensor.

In one embodiment, the biosensor is in the form of a photonic crystal biosensor. The sample molecule is labeled with a fluorescent material, such as quantum dot or organic fluorescent dye. The emission intensity of the fluorescent material is increased by over two orders of magnitude through the combined effects of enhanced near fields produced by the photonic crystal and the enhanced surface area provided by the nanorod-structured dielectric film that is deposited on top of the photonic crystal surface. The porous dielectric film serves to shift the location of resonant leaky modes of the photonic crystal more fully into the volume in which biomolecular binding can take place, thus resulting in sensitivity gains that are greater than the gain attributable to only the increase in available surface area.

The approach of depositing a thin film of porous dielectric structures (e.g., nanorods) may be applied to any enhanced fluorescence biosensor surface structure, including 1-dimensional photonic crystals, 2-dimensional photonic crystals, 3-dimensional photonic crystals, surface plasmon resonance surfaces, planar waveguides, and grating-coupled waveguides. The dielectric nanorod structures are fabricated on the surface of a biosensor by the glancing angle deposition technique (GLAD).

Glancing angle deposition (GLAD) is a physical deposition technique in which the angle between the incoming flux and the surface of the substrate is set to be typically less than 15°. When the mobility of addatoms is limited, a self-shadowing effect during deposition results in a highly porous film with a structure composed of isolated vertical rods (or other shape depending on whether rotation is occurring during deposition and whether any additional layers are deposited using a non-GLAD technique). In previous research, we have demonstrated how these nanorod films applied to the surface of label-free PC biosensors increases detection sensitivity by enhancing the available surface area for biochemical binding. We demonstrate herein the enhancement of fluorescence on a PC surface through application of a dielectric nanorod coating to the device. We demonstrate enhancement of up to 114 times in fluorescence intensity compared to an unpatterned glass slide. Similar benefits would be expected for other types of biosensors having the porous dielectric surface as described herein.

While the PC example below includes a porous dielectric surface made from deposited layer of $TiO_2$, examples of other materials are possible for forming the porous dielectric surface, including $Ta_2O_5$, SiN, $SiO_2$, ZnS, MgF, VO and $HfO_2$. Suitable materials for nanorods could be any dielectric material with low optical loss coefficient at the resonant wavelength of the photonic crystal.

In general terms, we have provided in this disclosure an improvement to a biosensor adapted for detection of a sample labeled with a fluorescent label, the biosensor having a surface upon which the sample is deposited, the improvement characterized in that the surface is in the form a porous dielectric structure, e.g., having a multitude of raised structures (e.g., nanorods) surrounded by adjacent spaces. In one specific embodiment, the biosensor comprises a photonic crystal biosensor having a periodic surface grating structure, wherein the porous dielectric structure comprises a structure made from a relatively high index of refraction material, and wherein the raised structures are in the form of nanorods. The porous dielectric structure has a thickness t of between 25 and 300 nm in exemplary embodiments.

In one specific embodiment, the photonic crystal biosensor is preferably constructed with a grating layer, e.g., replica molded epoxy which is formed on a substrate sheet of plastic or glass, a spacer layer comprising a layer of material deposited on the grating layer, a high index of refraction layer comprising a layer of relatively high index of refraction material deposited on the spacer layer, and wherein the porous dielectric structure is deposited on the high index of refraction layer.

In preferred embodiments, the porous dielectric structure is deposited using a glancing angle deposition technique. However, other deposition techniques could be used to result in a porous dielectric film or layer being formed on the surface of a biosensor.

As noted above, porous dielectric surfaces can be formed on other, non-PC biosensors. In one specific embodiment, the biosensor comprises a surface plasmon resonance sensor comprised of structures that include periodically modulated metal gratings, periodically modulated metal thin films, arrays of periodically spaced metal holes in a metal thin film, metal particles, and metal particle clusters. In another embodiment the biosensor is in the form of a planar waveguide. In another embodiment, the biosensor is in the form of a grating-coupled waveguide.

In another aspect, methods of detection of a sample are described, comprising the steps of: a) providing a sample having a fluorescent label bound to the sample; b) placing the sample onto a photonic crystal biosensor as described in this disclosure having a porous dielectric surface; c) illuminating the biosensor with light that excites the fluorescent label and capturing fluorescent emission from the sensor with a detection instrument; and d) determining the intensity of the fluorescence emission from the sensor. The illuminating step involves use of an optical source such as a laser, LED, mercury vapor lamp, or tungsten halogen lamp. The fluorescent emission from the fluorescent label is at a higher wavelength which is detected with a photomultiplier tube, imaging camera, or some other photon detection device. In a representative embodiment, the sample comprises a biological sample, e.g., DNA sample, virus, protein or protein fragment, etc. The sample can be labeled with any suitable fluorophore, such as an organic fluorophore or a luminescent semiconductor material known in the art as a "quantum dot."

In a further aspect of this disclosure, a method of manufacturing a biosensor is provided comprising the steps of providing a biosensor (e.g., PC sensor, Surface Plasmon Resonance sensor, planar waveguide, etc.) having an upper surface and depositing a porous dielectric structure deposited on the relatively high index of refraction layer on the upper surface of the biosensor. In this context, "relatively high index of refraction" means any material having an index of refraction n greater than that of water. In representative embodiments the depositing step is performed using a glanced angle deposition (GLAD) deposition technique. In a further representative embodiment, the porous dielectric surface is characterized as having a multitude of raised structures surrounded by adjacent spaces, wherein the raised structures comprise rod-like structures and wherein the porous dielectric structure has a thickness t of between 25 and 300 nm.

Alternatives to GLAD as a deposition technique are possible. Other methods such as electrochemical etching on silicon (see Lin et al., *A Porous Silicon-Based Optical Interferometric Biosensor*, Science Vol. 278 pp. 840-844 (October 1997)) and electrochemical deposition of porous gold and platinum films (see Wang et al., *Glucose oxidase entrapped in polypyrrole on high-surface-area Pt electrodes: a model platform for sensitive electroenzymatic biosensors*, Journal of Electroanalytical Chemistry vol. 575, pp. 139-146 (2005)) have also been shown to be able to create thin films with high surface area. Possible disadvantages of these methods include (1) they may not be applicable to dielectric materials such as titanium oxide (2) these methods may introduce contaminations into the films which may be not easily removed.

Photonic Crystal Example

Materials & Methods

Device Fabrication

A photonic crystal biosensor with porous dielectric surface is shown in cross-section in FIG. 2A. The biosensor 100 includes a substrate sheet 102 such as glass or plastic (e.g., polyester or polyethylene terepthalate), a relatively low index of refraction epoxy-cured one dimensional periodic surface grating 104 applied to the substrate 102, a $SiO_2$ spacer layer 106 deposited on the grating layer 104, a relatively high index of refraction $TiO_2$ layer 108 sputter deposited on the spacer layer 106, and the GLAD-coated porous layer 110 comprising a multitude of nanorods deposited on the high index layer 108.

The 1D grating layer structure 104 was fabricated on the substrate sheet 102 by a cost-effective nanoreplica molding process, described in the patent literature previously cited. In brief, electron-beam lithography was used to define on a Si "master" wafer, the negative image of the desired surface structure 104 pattern, in this case a linear grating with a period of $\Lambda=360$ nm and a grating depth of $t_1=60$ nm, as shown in FIG. 2A. A thin layer of liquid UV-curable epoxy (n=1.46) was then sandwiched between a flexible polyester substrate 102 and the master wafer. After the epoxy was cured, the polyester sheet 102 with the grating structure 104 was peeled away from the master wafer. A layer 106 of $SiO_2$ (refractive index n=1.46, $t_2\sim 350$ nm) was deposited onto the structure 104 by electron-beam deposition and a layer 108 of $TiO_2$ (n=2.25, $t_3=100$ nm) was sputtered onto the device surface. The device was then mounted onto a microscope slide using an optical adhesive. The layer 106 of $SiO_2$ with the same refractive index as the epoxy grating layer 104 acts as a spacer layer to separate the epoxy material, which exhibits a small amount of background fluorescence, and the high index of refraction TiO$_2$ layer 108, where the highest intensity of the near electric-fields at resonance occurs. As a result, the background fluorescence from the epoxy material can be minimized.

The structure described above is a fully functional photonic crystal sensor designed to support guided-mode resonances at designated wavelengths. When illuminated with TE polarized (electric field parallel to the grating lines, i.e. y-axis) light at an incident angle $\beta=6.0°$, the reflection spectrum consists of two resonant peaks, one at $\lambda=633$ nm which overlaps the output wavelength of a HeNe laser used to excite Cyanine-5 (Cy-5) fluorophore, and a second peak at $\lambda=694$ nm. The reflection spectrum of the PC device was measured with a transmission setup equipped with a broadband white light source, a polarizer to isolate the TE polarization and a UV-visible spectrometer. The result is shown as the curve 120 in FIG. 2B, where the $\lambda=633$ nm TE resonance has a full width at half maximum (FWHM) of $\Delta\lambda=19.5$ nm.

Nanorod Film Deposition

Figure 3A:
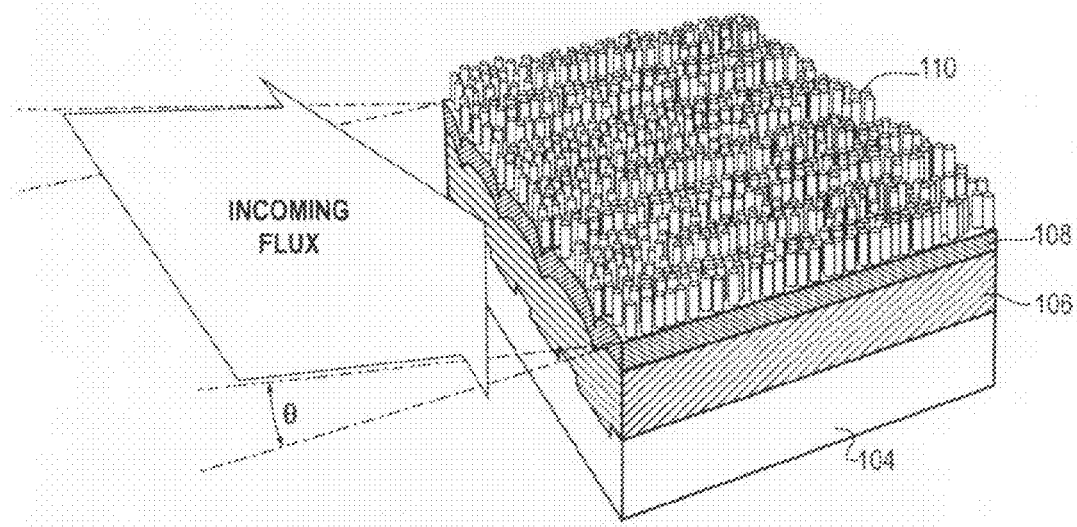
FIG. 3A is a schematic illustration of the GLAD deposition setup during which a thin film porous dielectric structure in the form of a multitude of nanorods are deposited on the sensor's surface to complete the manufacturing of the sensor.
Figure 3B:
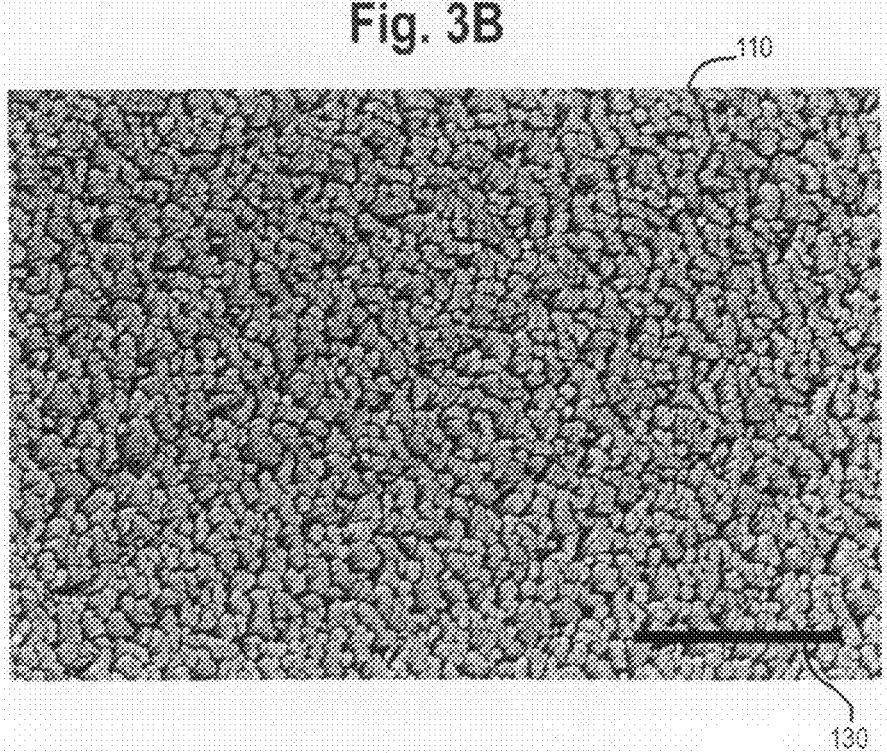
FIG. 3B is a scanning electron micrograph (SEM) illustration of a GLAD-coated device with a 70 nm-thick $TiO_2$ thin film porous dielectric structure in the form of a multitude of nanorods. The scale bar at the lower right of FIG. 3B represents 1 μm.

After PC device fabrication with dense TiO$_2$ film as described above, the GLAD technique was used to create the porous dielectric nanorod layer shown as layer 110 in the cross-section in FIG. 3A. The nanorod layer 110 is shown in perspective view in the illustration of FIG. 3A and in the SEM image of FIG. 3B. As can be seen in FIGS. 3A and 3B, the nanorod layer consists of a multitude of raised, rod-like structures extending upwardly from the high index layer 108, the rod-like structures separated from each other by adjacent spaces; in the aggregate and in a more macroscopic sense the surface is a porous surface in which the sample may be contained within the spaces between the individual rod-like structures.

We explored the effects of different thicknesses of nanorod structured TiO$_2$ deposited onto the device surface using an electron-beam deposition system (Temescal) with a base pressure of $1.0\times10^{-6}$ torr and a deposition rate of 10 Å/s. The angle between the incoming flux of evaporated material and the device surface was set to be $\theta=5.0°$, as shown in FIG. 3A. To minimize the shadowing effect between grating lines, the incoming flux was chosen to be parallel to the grating sidewalls and no substrate rotation was used during deposition. Also, no substrate heating was used in order to minimize the mobility of the addatoms. The refractive index of a nanorod film that was co-deposited on a Si wafer positioned next to the PC was measured by a spectroscopic ellipsometer (Woollam). Nanorod films with eight different thicknesses ranging from 25 to 277 nm were deposited upon PC devices that were previously prepared with a dense layer of TiO$_2$ applied by sputtering, as described above.

Simulation

Figure 5:
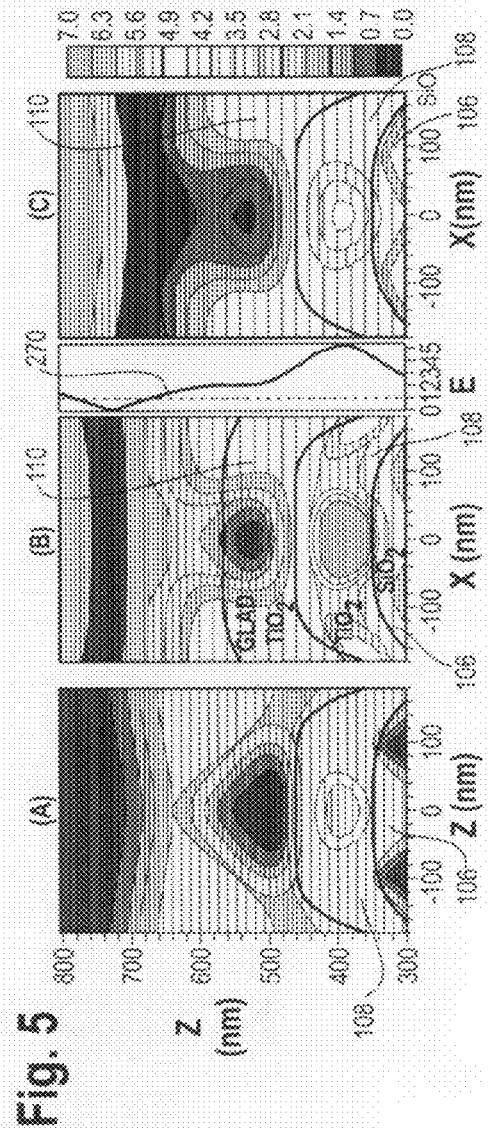
FIG. 5 illustrates plots of the calculated near electric field amplitude (E) for three photonic crystal sensors. In plot a) the sensor does not have a GLAD-deposited porous thin film; in plot b) the GLAD-deposited porous thin film $TiO_2$ layer is 105 nm thick; and in plot c) the GLAD-deposited porous thin film $TiO_2$ layer is 230 nm thick. The black lines in FIG. 5 show the upper boundaries of the sputtered $TiO_2$ and $TiO_2$ GLAD layers.

Commercial software (Rsoft) utilizing the rigorous coupled-wave analysis (RCWA) algorithm was used to simulate the behavior of PC devices with different thickness of nanorod coating. For the device without nanorod coating, a model of the device structure with dimensions in FIG. 2A was made and periodic boundary conditions were applied to the x extent. The transmission spectrum for illumination with incident light ($\beta=6.0°$, TE polarization, $-z$ direction) was calculated and plotted as the curve 122 in FIG. 2B, which has a good agreement with the experimentally measured data plotted as the curve 120. For devices with porous TiO$_2$ coatings, since the feature size of the nanorod structure is much smaller than the wavelength of visible light, Mie and Rayleigh scattering can be neglected and the nanorod layer is considered to be a uniform layer without any internal structure in the simulation. The near electric-field amplitude |E| was calculated as a function of nanorod thickness ranging from 0 to 300 nm and the results for 0, 105 and 230 nm of coatings are plotted in FIG. 5. To study the overall effect of the enhanced near fields to fluorophores uniformly distributed within the nanorod layer in the ideal case, the near electric-field intensity $E^2$ was calculated and a spatial average of the distribution of $E^2$ within the nanorod layer was taken. The FWHM of the 633 nm resonant peak was also calculated as a function of nanorod thickness.

To compare the fluorescence intensities of devices with different thickness of nanorod TiO$_2$ coatings, the devices were first functionalized with a proprietary polymer consisting of a long, narrow molecular chain with a high density of amine (NH$_2$) functional groups available along its backbone. For this step, the devices were incubated with a 1% solution of polymer in water for 26 hours, followed by washing with water. Next, the devices were immersed in a bifunctional linker, 25% of glutaraldehyde (C$_5$H$_8$O$_2$, Sigma-Aldrich) in water, for 6 hours, followed by a wash step. The last step of the protocol was to attach a fluorophore molecule to the device surface. Eight spots of 1 ul of Cy5-conjugated Streptavidin (10 μg/ml; GE healthcare) was hand-spotted onto the devices using a pipette and allowed to incubate for 30 hours, followed by a wash step.

The same protocol was also applied to an unpatterned microscope slide (left hand side of FIG. 4, image 204) which serves as a reference. Since the affinity of surface chemistry layers is different for different materials, in order to make a comparison, the reference slide was previously coated with an 18 nm of sputter deposited dense TiO$_2$.

After application of the Cy5-conjugated streptavidin spots, all devices were scanned at 20 μm pixel resolution in a fluorescence scanner (LS 2000, Tecan), equipped with a $\lambda=633$ nm laser. The incident light was TE polarized and had an incident angle of $\beta=6$ deg.

Results

The self-shadowing effect and limit on surface diffusion in the glancing angle deposition results in the formation of nanorod structures uniformly coated on the device surface, as shown in the SEM photo of FIG. 3B. The refractive index of the nanorod TiO$_2$ film is measured to be n=1.45 at a wavelength of 630 nm, while TiO$_2$ films deposited by evaporation in the same system at normal incidence or by sputtering have a refractive index of n=2.25. Therefore, assuming that the nanorod TiO$_2$ film contains a mixture of TiO$_2$ and air, we estimate that the film is comprised of 65:35 mixture of air: TiO$_2$, assuming a linear relation for a combination of two materials.

Figure 4:
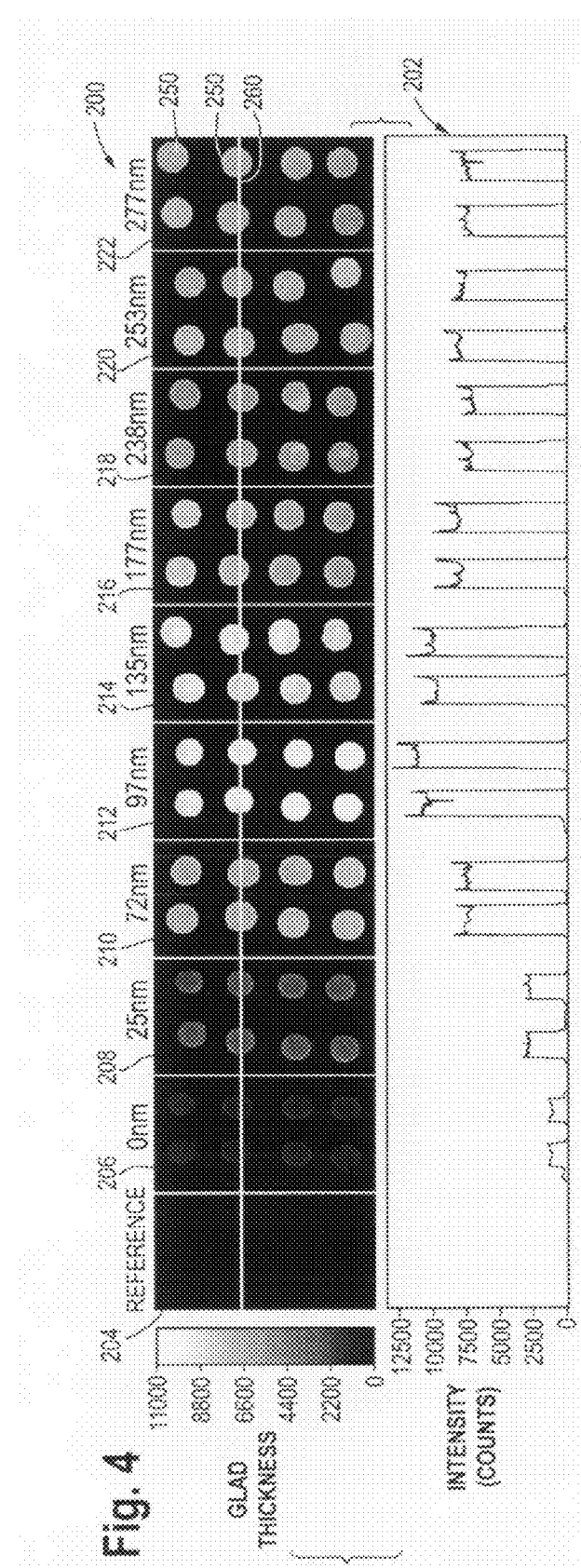
FIG. 4 is a series of images of Streptavidin/Cy5 spots, and intensity plots of reflected light for the spots in the series of images taken along the line through each of the images. The left-most image of the series is a control image in which the Streptavidin/Cy5 is deposited on a reference slide (unpatterned glass slide with 18 nm of sputter deposited $TiO_2$), and the remaining images shows images of spots on photonic crystal sensors with different thickness of GLAD-deposited nanorods. The photonic crystals with the 97 nm and 135 nm thick GLAD-deposited nanorods have the highest intensity counts as indicated by the brightest images of the spots and the highest intensities in the plots of reflected light.

FIG. 4 is a series of images 200 of Streptavidin/Cy5 spots 250, and intensity plots 202 of reflected light for the spots 250 in the series of images taken along the line 260 through each of the images. The left-most image 202 of the series 200 is a control image in which the Streptavidin/Cy5 is deposited on a reference slide (unpatterned glass slide with 18 nm of sputter deposited TiO$_2$), and the remaining images 206, 208, 210, 212, 214, 216, 218, 220 and 222 shows images of spots on photonic crystal sensors with different thickness of GLAD-deposited nanorods. The photonic crystals with the 97 nm and 135 nm thick GLAD-deposited nanorods (images 212 and 214) have the highest intensity counts as indicated by the brightest images of the spots and the highest intensities in the plots 202 of reflected light.

The images of Cy5-conjugated streptavidin spots on all the devices including the reference slide are shown in FIG. 4. A line profile of the fluorescence intensity across all devices is taken along line 260 and plotted in the intensity plots 202 of FIG. 4. After background subtraction, the highest average signal of 11123 counts within 8 spots was obtained from the device with 97 nm of nanorod $TiO_2$ coating. This is over 114× the enhancement when compared to the signal of the reference unpatterned microscopy slide (image 204) which had an average intensity of 97 counts. As a function of nanorod $TiO_2$ thickness, the fluorescence intensity increases gradually from 0 nm (1231 counts) up to 97 nm (11123 counts), then starts to decrease slowly until it reaches a plateau at 238 nm (6955 counts). At the maximum nanorod $TiO_2$ thickness of all the devices, 277 nm, the average intensity is 7290 counts. While nanorod thicknesses (depth of the layer 110) up to 277 nm were tested in this example, greater thicknesses are possible. In general, useful PC sensors are envisioned with thicknesses of the nanorod layer in the range of 25 to 300 nm, with ranges between 70 and 300 nm being consider a preferred range.

Discussion

In order to make a rough estimate of the surface area available due to the nanorod $TiO_2$ film, a simplified physical model was constructed based on the ellipsometry measurements of $TiO_2$ density. If we assume that the nanorod $TiO_2$ film of thickness $t_4$ (FIG. 2A) consists of rods with the same diameter, arranged in a square lattice with equal spacing between adjacent rods, a film with a 65:35 air:$TiO_2$ ratio is obtained with a rod diameter of D=30 nm and a gap of g=15 nm between adjacent rods. The extra surface area provided by each "rod" is the area of the sidewall which is equal to $\pi D t_4$. The ratio of the total surface area of such a film over that of a flat surface is then given by $$areafactor = \frac{\pi D t_4 + (D+g) \times (D+g)}{(D+g) \times (D+g)} = 1 + \frac{30\pi}{45^2} \times t_4 \quad (1)$$

Figure 6A:
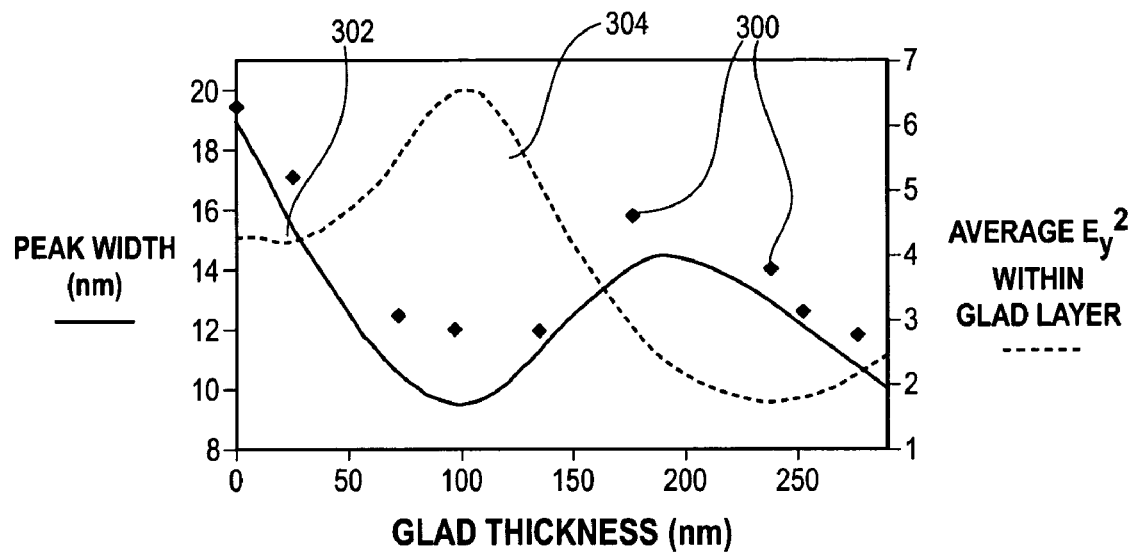
FIG. 6A is a plot of the measured and calculated full width half maximum (FWHM) of the 633 nm resonant peak, and calculated average of the near electric field intensity ($E^2$) within GLAD layers for devices as a function of the thickness of the GLAD layers.
Figure 6B:
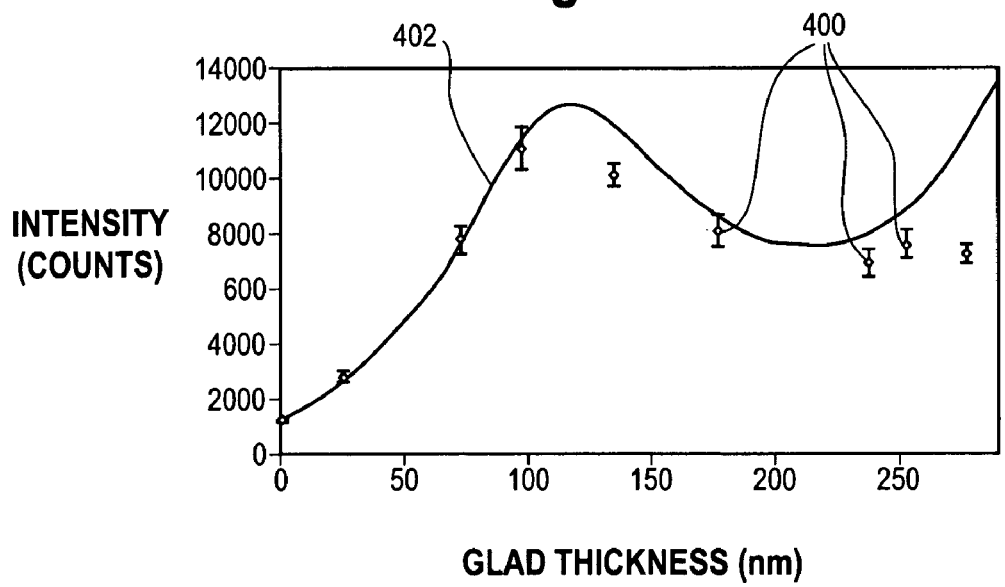
FIG. 6B is a plot of the measured fluorescence intensity (dots with error bar showing N=8) and simulated intensities (line) as a function of GLAD thickness.

The overall enhancement of fluorescence intensity comes from a combination of enhanced near electric-fields and enhanced surface area. FIG. 6A is a plot of the measured and calculated full width half maximum (FWHM) of the 633 nm resonant peak, and calculated average of the near electric field intensity ($E^2$) within GLAD layers for devices, plotted as a function of the thickness of the GLAD layers. Assuming the fluorophores are uniformly distributed within the nanorod layers, we expect the product of average $E^2$ within the nanorod layer (line 304 in FIG. 6A) and the areafactor (given by Equation 1) would be a reasonable figure of merit describing how the total enhancement changes with nanorod thickness. In order to compare with experimental fluorescent intensity, this product is calculated as a function of nanorod thickness and normalized to the experimentally measured fluorescent intensity of PC with 0 nm of nanorod (1231 counts). FIG. 6B is a plot of the measured fluorescence intensity (dots with error bar showing N=8) and simulated intensities (line) as a function of GLAD thickness. The simulated result is plotted as the line 402 in FIG. 6B and we see an excellent agreement with the measured intensities shown as the dots 400.

Further analysis of the relationship between fluorescence intensity and nanorod thickness reveals that the trend shown in FIG. 6B may be explained by three effects introduced by the nanorod dielectric layers, which here we refer to as surface area, Q-factor, and near field distribution.

The first effect of surface area is explained by Equation 1; the total surface area of nanorod coating increases linearly with thickness, assuming the simplified model mentioned above. In reality, as the nanorod thickness increases, it becomes more and more difficult for the surface chemistry molecules and fluorophores to diffuse into the bottom regions of the film and fully utilize the extra surface area. Furthermore, the observed degree of taper in the nanorod structure also increases with thickness, which makes the diffusion of molecules even more difficult. These factors might explain the deviation of experimental data above 200 nm from the predicted curve in FIG. 6B.

The second effect of Q-factor is related to the fact that the introduction of nanorod coating changes the RI of the superstrate of PC, thus changing the quality of the resonance and the overall magnitude of the near fields. As shown in FIG. 6A of both the simulated and experimental data, as indicated by the line 302 and the points 300, the FWHM of the 633 nm resonant peak decreases as nanorod thickness increases until it reaches a minimum at about 105 nm. Then the FWHM starts increasing until it peaks at about 200 nm of nanorod thickness where the trend starts to reverse again. Since the FWHM of the resonant dip is inversely proportional to the Q-factor of the resonance, we expect the quality of resonance and therefore the overall magnitude of near fields to have an opposite trend to the line 304 in FIG. 6A. This is confirmed by the calculated field distributions shown in FIG. 5: a PC coated with 105 nm of nanorod (illustration b)) has much higher E compared to PCs with 0 (illustration (a)) and 200 nm (illustration (c)).

The last effect, near-field distribution, results from the fact that fluorophores within the nanorod layer have a chance to interact with additional regions of the near field resonant mode distribution since the nanorod structure extends the surface area for binding into a 3D volume. As shown in FIG. 4, although the overall magnitude of the near electric-field changes with nanorod thickness, the pattern of distribution remains about the same. The curve 270 in FIG. 4 shows the average |E| across x direction as a function of the vertical dimension, z. The most intense near electric-field is positioned in the high refractive index layer of sputtered $TiO_2$, above which |E| decreases with z. Since |E| is above 1 V/m, which is the normalized incident light amplitude, fluorophores in this region will have enhanced emission intensity and increasing the nanorod thickness will increase the total fluorescent intensity. Once the nanorod thickness reaches about 208 nm (z=671 nm), the film enters the node of the near field distribution of the standing wave interference pattern above the PC structure. Further increase of the nanorod thickness will not be very effective in further enhancing the total fluorescence intensity since |E| in this region is below 1 V/m. The combined effect of Q-factor and near field distribution is represented by the average $E^2$ within the nanorod layer plotted as the line 304 in FIG. 6A.

Such a fluorescence enhancement scheme combing a PC structure and a high surface-area coating with nanometer-scale dimensions can be invaluable to the future design of devices. Since the nanorod structure extends the available surface area into a 3D volume, the whole volume instead of the very first layer of the near fields is used to enhance the excitation of the fluorophores. The Q-factor of the PC reported in this study is relatively low (Q~33) and future work will focus on combing PC design of high Q-factor (as high as ~2000 demonstrated) with high surface area nanorod structures to achieve even higher fluorescent intensity enhancement.

We have demonstrated the enhancement of fluorescence intensity of fluorophores on a PC surface coated with a nanorod structured $TiO_2$ film. Up to 114× enhancement in intensity has been shown and the enhancement is a result of the enhanced near electric-field from the resonance of PC structure and the enhanced surface area provided by the nanorod layer.

From the foregoing, it will be appreciated that we have disclosed a photonic crystal biosensor comprising: a substrate layer, a periodic grating applied to the substrate layer; a relatively high index of refraction layer deposited on the periodic grating layer; and a porous dielectric structure deposited on the relatively high index of refraction layer, the porous dielectric structure comprises a structure made from a relatively high index of refraction material.

In one configuration the thickness t of the porous dielectric structure is between 25 and 300 nm.

In one embodiment, the biosensor is incorporated into a sample handling device, such as a microscope slide, multi-well plate or other convenient handling device adapted to handle a fluid sample.

In a representative and non-limiting embodiment, the porous dielectric layer of the photonic crystal sensor is characterized as having a multitude of raised structures surrounded by adjacent spaces, and wherein the raised structures comprise rod-like structures.

While presently preferred embodiments have been described with particularity, variation from the specifics of the disclosed embodiments is possible without departure from the scope of the invention. All questions concerning scope are to be answered by reference to the appended claims.

We claim:

1. In a photonic crystal biosensor adapted for detection of a sample labeled with a fluorescent label, the biosensor having a periodic surface grating structure and a dielectric material deposited on the periodic surface grating structure, the dielectric material providing a surface upon which the sample is deposited, the improvement comprising:
   the surface of the biosensor comprising a porous dielectric structure in the form of a multitude of closely spaced raised structures made from a dielectric material, wherein the closely spaced raised structures are surrounded by adjacent spaces, and wherein the raised structures and adjacent spaces providing an enhanced surface area available for binding of the sample to the biosensor.

2. The improvement of claim 1, wherein the closely spaced raised structures comprises a multitude of nanorods having has a thickness t of between 25 and 300 nm.

3. The improvement of claim 1, wherein the photonic crystal biosensor further comprises a spacer layer comprising a layer of material deposited on the periodic surface grating structure, a high index of refraction layer comprising a layer of relatively high index of refraction material deposited on the spacer layer, and wherein the porous dielectric structure as recited in claim 1 is deposited on the high index of refraction layer.

4. The improvement of claim 1, wherein the porous dielectric structure comprises a multitude of nanorods.

5. In a surface Plasmon resonance biosensor, adapted for detection of a sample, the improvement comprising:
   a porous dielectric structure deposited on the surface Plasmon resonance biosensor, the porous dielectric structure providing a surface upon which the sample is deposited, and wherein the porous dielectric structure comprises a multitude of nanorods made from a dielectric material surrounded by adjacent spaces, the dielectric nanorods and adjacent spaces providing an enhanced surface area available for binding of the sample to the biosensor.

6. In a planar waveguide, adapted for detection of a sample, the improvement comprising:
   a porous dielectric structure deposited on the planar waveguide, the porous dielectric structure providing a surface upon which the sample is deposited, wherein the porous dielectric structure comprises a multitude of nanorods made from a dielectric material surrounded by adjacent spaces, the nanorods and adjacent spaces providing an enhanced surface area available for binding of the sample to the planar waveguide.

7. In a grating-coupled waveguide, adapted for detection of a sample, the improvement comprising:
   a porous dielectric structure deposited on the grating-coupled waveguide, the porous dielectric structure providing a surface upon which the sample is deposited, and wherein the porous dielectric structure comprises a multitude of nanorods made from a dielectric material surrounded by adjacent spaces, the nanorods and adjacent spaces providing an enhanced surface area available for binding of the sample to the grating-coupled waveguide.

8. A photonic crystal biosensor comprising:
   a substrate layer;
   a periodic grating applied to the substrate layer;
   a relatively high index of refraction layer deposited on or above the periodic grating layer; and
   a porous dielectric structure comprising a dielectric material deposited on the relatively high index of refraction layer, the porous dielectric structure in the form of a multitude of closely spaced raised structures made from said dielectric material, the closely spaced raised structures surrounded by adjacent spaces, the raised structures and adjacent spaces providing an enhanced surface area available for binding of the sample to the biosensor.

9. The photonic crystal biosensor of claim 8, wherein the thickness t of the porous dielectric structure is between 25 and 300 nm.

10. The photonic crystal biosensor of claim 8, wherein the biosensor is incorporated into a sample handling device.

11. The photonic crystal biosensor of claim 8, wherein the raised structures comprise nanorods.

12. A method of detection of a sample comprising the steps of:
   a) providing a sample having a fluorescent label bound to the sample;
   b) placing the sample onto a biosensor as claimed in claim 8;
   c) illuminating the biosensor with light in a manner to excite the fluorescent label and capturing the fluorescence emission from the biosensor with a detection instrument; and
   d) determining the intensity of the fluorescent emission from the biosensor.

13. The method of claim 12, wherein the sample comprises a biological sample.

14. The method of claim 12, wherein the label comprises an organic fluorophore.

15. The method of claim 12, wherein the label comprises a quantum dot.

16. A method of manufacturing a biosensor comprising the steps of:
   providing a biosensor having an upper surface; and
   depositing a dielectric material on the upper surface of the biosensor so as to form a porous dielectric structure, the porous dielectric structure forming a surface for receiving a sample deposited on the biosensor, the porous dielectric structure in the form of a multitude of closely spaced raised structures made from a dielectric material, the closely spaced raised structures surrounded by adjacent spaces, the raised structures and adjacent spaces providing an enhanced surface area available for binding of the sample to the biosensor.

17. The method of claim 16, wherein the depositing step is performed using a glanced angle deposition (GLAD) deposition technique.

18. The method of claim 16, wherein the biosensor comprises a substrate layer, a periodic grating applied to the substrate layer, a relatively high index of refraction layer deposited on the periodic grating layer and forming the said upper surface, and wherein in the depositing step further comprises the step of depositing the porous dielectric structure on the relatively high index of refraction layer.

19. The method of claim 16, wherein the raised structures comprise nanorods and wherein the porous dielectric structure has a thickness t of between 25 and 300 nm.

20. The photonic crystal biosensor of claim 8, wherein the dielectric material comprises a dielectric material having a low optical loss coefficient at a resonant wavelength of the photonic crystal.

21. The photonic crystal biosensor of claim 20, wherein the dielectric material is selected from the groups of materials consisting of $TiO_2$, $Ta_2O_5$, SiN, $SiO_2$, ZnS, MgF, VO and $HfO_2$.

* * * * *